United States Patent [19]

Mullins

[11] 4,431,592

[45] Feb. 14, 1984

[54] UNSATURATED ESTERS AND METHOD OF PREPARATION

[75] Inventor: Michael J. Mullins, Midland, Mich.

[73] Assignee: The Dow Chemical Company, Midland, Mich.

[21] Appl. No.: 371,767

[22] Filed: Apr. 26, 1982

[51] Int. Cl.³ .................. C07C 67/343; C07C 69/24; C07C 69/28; C07C 69/74

[52] U.S. Cl. .................. 260/410.6; 260/410.9 R; 560/122

[58] Field of Search .............. 560/122; 260/410.6, 260/410.9 R

[56] References Cited

U.S. PATENT DOCUMENTS 4,091,226  5/1978  Buendia et al. .................. 560/122
4,180,676  12/1979  Stapp .............................. 560/122 X

FOREIGN PATENT DOCUMENTS 48-34572 of 1973 Japan.

OTHER PUBLICATIONS

P. W. Jolly et al., The Organic Chemistry of Nickel, vol. 2, Academic Press, pp. 187-196, 200-212 (1975).
S. Akutagawa, Bull. Chem. Soc. Japan, 49, 3646 and 3648 (1976).

*Primary Examiner*—Natalie Trousof
*Assistant Examiner*—Vera C. Clarke
*Attorney, Agent, or Firm*—Douglas N. Deline

[57] ABSTRACT

Novel unsaturated esters having utility as cross-linking agents and in the formation of polymers are prepared by reacting a diene with a cyclic alkylene carbonate in the presence of a catalyst comprising a zero valent nickel-phosphine complex at a temperature from about 50° C. to about 200° C.

13 Claims, No Drawings

UNSATURATED ESTERS AND METHOD OF PREPARATION

BACKGROUND OF THE INVENTION

The present invention relates to a process for the preparation of esters. More particularly the present invention relates to a process whereby a diene is reacted with an alkylene carbonate. The ester-containing products prepared according to the present invention are useful cross-linking agents in polymeric systems such as polystyrene. In addition, the compounds may be homopolymerized to prepare solid polymeric products or used as intermediates for the preparation of other commercially valuable compounds such as pharmaceuticals and perfumes.

SUMMARY OF THE INVENTION

The present invention provides novel unsaturated esters or mixtures thereof corresponding to the formula:

XC(O)OR' wherein
X is

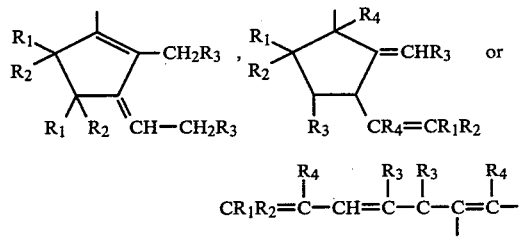

where $R_1-R_4$ independently each occurrence are selected from the group consisting of hydrogen, halogen and $C_{1-20}$ hydrocarbyl; and R' is $C_{1-6}$ alkyl, $-CH_2CHR_5OH$ or $-CH_2CHR_5OC(O)X$ where $R_5$ is hydrogen, halogen or $C_{1-20}$ hydrocarbyl, and X is as previously defined.

Also included in the present invention is a novel method of preparing the above unsaturated esters wherein R' is $-CH_2CHR_5OH$ comprising contacting a diene corresponding to the formula:

$CR_1R_2=CR_4-CH=CHR_3$ with a cyclic alkylene carbonate of the formula:

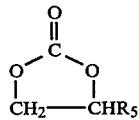

wherein $R_1-R_5$ are as previously defined in the presence of a catalyst comprising a zero valent nickel-phosphine complex at a temperature from about 50° C. to about 200° C. for a time sufficient to prepare substantial quantities of the above identified unsaturated ester.

DETAILED DESCRIPTION OF THE INVENTION

The dienes suitable for use according to the present invention are conjugated dienes optionally containing the substituents previously noted. Preferred are well-known conjugated dienes that are readily available industrially wherein one of $R_1-R_4$ may be methyl and the remaining substituents are all hydrogen. Most preferred diene reactants include 1,3-butadiene, 1,3-pentadiene or isoprene or mixtures thereof. Accordingly, the unsaturated esters prepared therefrom preferably have one of $R_1-R_4$ either hydrogen or methyl and the remaining substituents are hydrogen.

The dienes may be employed in a purified form or used as mixtures with other gases that are unreactive under the reaction conditions employed. It is seen that the reaction generally requires two moles of diene reactant for every mole of cyclic alkylene carbonate. The cyclic alkylene carbonates for use according to the present invention are preferably those wherein $R_5$ of the formula provided is hydrogen or $C_{1-4}$ alkyl. Most preferred cyclic alkylene carbonates are ethylene and propylene carbonate.

Suitable catalysts for the invented process are selected from zero valent nickel phosphine complexes capable of catalyzing the reaction. Preferred phosphines are organo phosphines of the formula $(R)_3P$ wherein R is phenyl or $C_{1-10}$ alkyl. A most preferred phosphine is triethyl phosphine.

The process may be conducted in a solvent or neat. Suitable solvents include polar organic compounds such as tetrahydrofuran, ethylene glycol, ethylene glycol monoalkyl ether, glyme, diglyme, etc., and mixtures thereof. A preferred solvent is tetrahydrofuran.

The process is conducted at elevated temperatures from 100° C. to about 150° C., depending on the solvent system and reactants employed. At lower temperatures the reaction rate tends to diminish, while at elevated temperatures above about 150° C., the catalyst tends to degrade due to thermal instability. A preferred temperature is from about 110° C. to about 130° C.

The reaction may be conducted at elevated or reduced pressures or at atmospheric pressure, depending primarily on the partial pressure of the olefin reactant. In particular, where the temperature employed exceeds the normal boiling point of the solvent system, it will be necessary to employ elevated pressures.

Continued heating of the reaction product results in condensation of the unsaturated ester product thereby forming a bis ester of the formula $XC(O)OCH_2CHR_5O(O)CX$ and release of an aliphatic diol. Thus, it is possible upon heating of the reaction product of ethylene glycol and butadiene for example, to prepare ethylene glycol plus the bis ester of the formula:

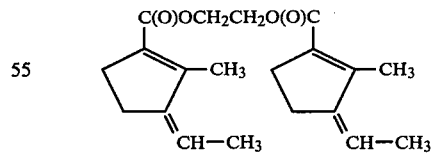

Such bis esters constitute one embodiment of the present invention.

The stability of the products and thus their utility in such applications as cross-linking agents may be enhanced by substitution of a less reactive ester group for the β-hydroxy-containing ester functionality originally prepared by the process. The substitution is readily accomplished under transesterification conditions by reaction of the ester product including the above bis esters with a $C_{1-6}$ alcohol such as methanol or ethanol. Accordingly, the product prepared will be a compound of the formula XC(O)OR' where R' is $C_{1-6}$ alkyl and X is as previously defined.

SPECIFIC EMBODIMENTS

Having described my invention the following examples are provided as further illustrative of the present invention and are not to be construed as limiting.

EXAMPLE 1

1,2-Ethanediyl bis-(3-ethylidene-2-methyl-1-cyclopentene-1-carboxylate)

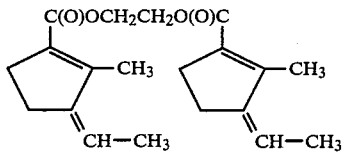

A 200-ml stainless steel autoclave was filled in an argon atmosphere with the following: ethylene carbonate (11.01 g, 0.125 mole), tetrahydrofuran (25 ml), Ni[1,5-cyclooctadiene]$_2$ (300 mg, 1.09 mmole) and triethylphosphine (800 mg, 6.78 mmole). The autoclave was sealed, weighed to the nearest 0.1 g in air, and charged with butadiene (31.5 g net weight, 0.583 mole). The autoclave was then heated to 120° C. for 17 hours. During the reaction, the pressure inside the autoclave rose to about 215 psig. After heating for the indicated time period, the autoclave was cooled and vented. The product mixture comprised a yellow-green solution that was evaporated and then slowly distilled (150° C., 1 torr.) to remove butadiene oligomers, unreacted ethylene carbonate and ethylene glycol.

Analysis of the reaction product indicated a major component was 2-hydroxyethyl 3-ethylidene-2-methyl-1-cyclopentene-1-carboxylate. Continued bulb to bulb distillation of the reaction product (air bath, 220° C. at 0.2 torr) resulted in the production of further amounts of ethylene glycol and a pale yellow oil that crystallized upon standing. An analytical sample obtained by recrystallization from hexane was identified as the desired product 1,2-ethanediyl bis-(3-ethylidene-2-methyl-1-cyclopentene-1-carboxylate). mp. 95° C.–97° C.

EXAMPLE 2

2-Hydroxyethyl 2,5-dimethyl-3-(1-propenyl)-1-cyclopentene-1-carboxylate

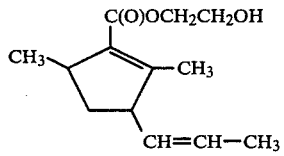

A 200-ml stainless steel autoclave was filled in an argon atmosphere with the following: ethylene carbonate (22.0 g, 0.25 mole), 1,3-pentadiene (E and Z mixture, 50.0 ml, 0.50 mole), tetrahydrofuran (50 ml), Ni[1,5-cyclooctadiene]$_2$ (300 mg, 1.09 mmole) and triethylphosphine (515 mg, 4.36 mmole). The autoclave was sealed and heated to 120° C. for 18 hours. The resultant yellow-green solution was evaporated and the title compound was isolated using column chromatography. Isolated yield was 11.19 g (20 percent of theory) of an isometric mixture containing 80 percent by weight of the title compound. Analysis by nuclear magnetic resonance spectroscopy confirmed the product's identity.

EXAMPLE 3

2-Hydroxyethyl 1-methyl-2-methylene-3-isopropenyl cyclopentane carboxylate

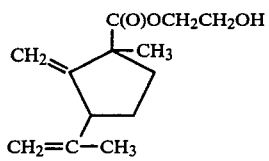

The reaction conditions of Example 1 were substantially repeated except that isoprene (10.21 g, 0.150 mole) was used in place of butadiene. The crude reaction material was evaporated and distilled at 140° C. at 1 mm. The pot residue was then bulb to bulb distilled (210° C. air bath at 0.6 mm) to give 9.27 g of a viscous yellow oil. This material is a mixture (~50:50) of the title compound and 2-hydroxyethyl 3-(2,7-dimethyl-2,5,7-octatriene)carboxylate:

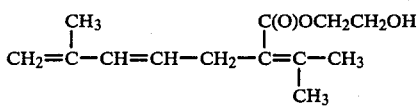

EXAMPLE 4

The bis ester of Example 1, 1,2-ethanediyl bis-(3-ethylidene-2-methyl-1-cyclopentene-1-carboxylate), was polymerized in a small test tube. Accordingly, a mixture of 0.42 g of the crystalline glycol diester and 0.05 g of dibenzoyl peroxide in a test tube was immersed in an oil bath maintained at 80° C. for 65 hours. The resulting solid casting was translucent, amber in color, slightly sticky and conformed in shape to the original test tube. The product was insoluble in hexane but soluble in methylene chloride.

What is claimed is:

1. An unsaturated ester corresponding to the formula:

wherein:
X is:

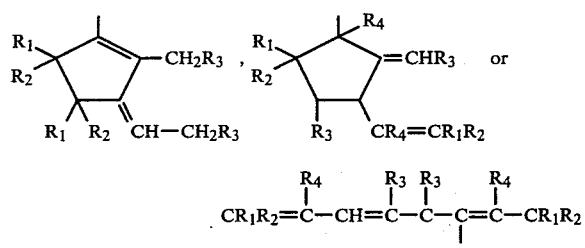

where $R_1$–$R_4$ independently each occurrence are selected from the group consisting of hydrogen, halogen, and $C_{1-20}$ hydrocarbyl; and R' is $C_{1-6}$ alkyl, —CH$_2$CHR$_5$OH or —CH$_2$CHR$_5$OC(O)X where R$_5$ is hydrogen, halogen or $C_{1-20}$ hydrocarbyl, and X is as previously defined.

2. An unsaturated ester according to claim 1 wherein one of R$_1$–R$_4$ is hydrogen or methyl and the remaining substituents are hydrogen.

3. An unsaturated ester according to claim 2 wherein R$_5$ is hydrogen or $C_{1-4}$ alkyl.

4. An unsaturated ester according to claim 3 wherein R$_5$ is hydrogen or methyl.

5. An unsaturated ester according to claim 1 that is 1,2-ethanediyl bis-(3-ethylidene-2-methyl-1-cyclopentene-1-carboxylate, 2-hydroxyethyl 3-ethylidene-2-methyl-1-cyclopentene-1-carboxylate, 2-hydroxyethyl 2,5-dimethyl-3-(1-propenyl)-1-cyclopentene-1-carboxylate, 2-hydroxyethyl 1-methyl-2-methylene-3-isopropenyl cyclopentane carboxylate, 2-hydroxyethyl 3-(2,7-dimethyl-2,5,7-octatriene)carboxylate, or mixtures thereof.

6. A process for preparing unsaturated esters corresponding to the formula:

XC(O)OR' wherein:
X is:

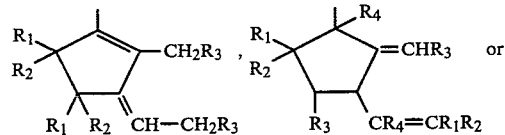

-continued

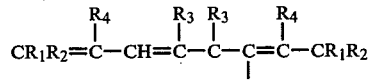

where R$_1$–R$_4$ independently each occurrence are selected from the group consisting of hydrogen, halogen, and $C_{1-20}$ hydrocarbyl; and R' is —CH$_2$CHR$_5$OH where R$_5$ is hydrogen, halogen or $C_{1-20}$ hydrocarbyl, comprising contacting a diene corresponding to the formula: CR$_1$R$_2$=CR$_4$—CH=CHR$_3$ with a cyclic alkylene carbonate corresponding to the formula:

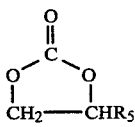

wherein R$_1$–R$_5$ are as previously defined,
in the presence of a catalyst comprising a zero valent nickel-phosphine complex at a temperature from about 100° C. to about 150° C. for a time sufficient to prepare substantial quantities of the unsaturated ester.

7. The process of claim 6 wherein the phosphine is of the formula (R)$_3$P wherein R is phenyl or $C_{1-10}$ alkyl.

8. The process of claim 7 wherein R is ethyl.

9. The process of claim 6 wherein the temperature is from about 110° C. to about 130° C.

10. The process of claim 6 wherein the diene is 1,3-butadiene, 1,3-pentadiene, isoprene or mixtures thereof.

11. The process of claim 6 wherein the cyclic alkylene carbonate reactant is ethylene or propylene carbonate.

12. The process of claim 6 wherein in addition a solvent is present.

13. The process of claim 12 wherein the solvent is tetrahydrofuran.

* * * * *